(12) United States Patent
DeMeester et al.

(10) Patent No.: US 6,922,580 B2
(45) Date of Patent: Jul. 26, 2005

(54) BLOOD FLOW GATED MRI

(75) Inventors: Gordon D. DeMeester, Wickliffe, OH (US); Kecheng Liu, Solon, OH (US)

(73) Assignee: Koninklijke Philips Electronics N.V., Eindhoven (NL)

(*) Notice: Subject to any disclaimer, the term of this patent is extended or adjusted under 35 U.S.C. 154(b) by 431 days.

(21) Appl. No.: 10/162,379

(22) Filed: Jun. 4, 2002

(65) Prior Publication Data

US 2003/0225328 A1 Dec. 4, 2003

(51) Int. Cl.⁷ .................................................. A61B 5/05
(52) U.S. Cl. ....................................... 600/413; 600/419
(58) Field of Search ................................. 600/413, 419, 600/410, 407; 324/306, 307, 300, 309, 314, 313, 311

(56) References Cited

U.S. PATENT DOCUMENTS

| | | | | |
|---|---|---|---|---|
| 5,031,624 A | * | 7/1991 | Mistretta et al. | 600/419 |
| 5,070,876 A | * | 12/1991 | Wright | 600/419 |
| 5,133,357 A | * | 7/1992 | Dumoulin et al. | 600/413 |
| 5,233,298 A | * | 8/1993 | Dumoulin | 324/306 |
| 5,435,303 A | * | 7/1995 | Bernstein et al. | 600/413 |

FOREIGN PATENT DOCUMENTS

EP  1 055 935 A2  11/2000

OTHER PUBLICATIONS

Hofman, et al. "Assessment of Flow in the Right Human Coronary Artery By Magnetic Resonance Phase Contrast Velocity Measurement: Effects of Cardiac and Respiratory Motion", MRM 35:521–531 (1996) XP000587723.

Langerak, et al. "Evaluation of Coronary Artery Bypass Grafts By Magnetic Resonance Imaging", Journ. Of Magnetic Resonance Imaging 10:434–441 (1999) XP009010955.

* cited by examiner

*Primary Examiner*—Daniel Robinson
(74) *Attorney, Agent, or Firm*—Faye Sharpe, Fagan, Minnich & McKee LLP

(57) ABSTRACT

A magnetic resonance imaging method and apparatus includes a navigator region defined within the subject by selective excitation. Blood flow is measured within the selected region using the principles of phase contrast MR angiography. A cardiac cycle plot is constructed from Fourier transformed data that represents measured velocity of blood flow through the navigator region as a function of time. On the basis of the cardiac cycle plot and the navigator measurements, data acquisition is synchronized or gated to portions of the cardiac cycle.

18 Claims, 2 Drawing Sheets

BLOOD FLOW GATED MRI

BACKGROUND OF THE INVENTION

The present invention relates to the magnetic resonance imaging arts. It finds particular application in conjunction with imaging triggered from the cardiac cycle and will be described with particular reference thereto. It is to be appreciated, however, that the present invention may also find application in other cardiac gated applications, gated imaging triggered by other moving fluids or tissues, and the like.

In magnetic resonance imaging, a substantially uniform main magnetic field is generated within an examination region. The main magnetic field polarizes the nuclear spin system of a patient being imaged within the examination region. Magnetic resonance is excited in the polarized region by $B_1$ fields generated from radio frequency excitation signals throughout the examination region. Specifically, radio frequency pulses tip the dipoles out of alignment with the main magnetic field and cause the macroscopic magnetic moment to precess around an axis parallel to the main magnetic field. The precessing magnetic moment, in turn, generates a corresponding radio frequency magnetic resonance signal as the magnetic moment transverse to the direction of the main field relaxes. Magnetic field gradients are applied during this process to encode spatial information in the phase and frequency of the resonance signal. Movement of imaged tissue and the flowing of blood or other fluids disrupts the spatial encoding. The radio frequency magnetic resonance signal is received by the radio frequency coil assembly. From the spatial encoding of the received signals, an image representation is reconstructed for display on a human viewable display.

In cardiac imaging, one of the biggest problems is collecting data when the heart is not moving. If image data gathering is distributed over the whole cardiac cycle, the resultant image is reconstructed from all positions of the heart over the cardiac cycle. Therefore, it is desirable to take multiple image data snapshots from a fixed time segment within the cardiac cycle, so that when the snapshots are combined into a complete data set, the reconstructed image appears as if a still shot were taken of the heart. Selective imaging based on the phase of the cardiac cycle is known as cardiac gating. In addition to imaging the heart, cardiac gating is also useful in imaging regions remote from the heart that are affected by blood flow surges. For instance, an image of a region of the brain that includes an artery, an aneurysm, or other structure that changes with the cardiac cycle is gated.

In order to achieve such images, cardiac activity is monitored and data collection is synchronized with some feature of a monitored signal. In one method of cardiac gating, the pulse of the subject is monitored with an optical transducer placed on a finger of the subject. Light transmission through the finger varies with blood flow. A light signal maximum triggers the collection of data. A fixed delay is introduced to center data collection in other parts of the cardiac cycle. In practice, several factors can affect the timing of the cardiac cycle, for instance, comfort of the subject, health of the subject, distance of the imaged region from the heart, and other factors.

Another method of cardiac gating involves triggering from an electro-cardio-graph (ECG) signal. Typically, three or more electrodes are positioned on the chest of the subject to detect the electrical signals from the brain that control the heart. Each cycle of a normal ECG signal has an acute spike that represents the signal directing the left ventricle to contract. Shortly thereafter, the left ventricle contracts. Typically, in ECG triggered MRI, image data is collected commencing at a time point and continuing for a selected time interval.

Several disadvantages arise from using the ECG signal to trigger magnetic resonance imaging. Metal electrodes and lead wires are used to detect the electrical signal. The electrodes and lead wires cause local abnormalities in the magnetic field, and can distort images. Also, the radio frequency and gradient pulses can induce currents that generate electrode heating which can burn the patient. Extreme electrode heating can burn the patient. The ECG signal is subject to weakening and distortion from several sources, notably, surface resistance, physical condition of the subject, quality of pre-amplifiers, and other external sources. These sources weaken or corrupt the ECG signal making it non-representative of the heart activity in some cases. Additionally, the subject may be sick and not have a strong ECG signal. There are some windows of time where the ECG signal cannot be used as an accurate trigger, for instance in the time immediately preceding the main R-wave spike. It is difficult to obtain an ECG signal during data acquisition, when gradient and RF fields are active. Often the ECG signal is blanked at these times. Also, 1.5 and 3 Tesla magnetic fields distort and interact with the electrical activity making it difficult to detect a useful ECG signal. All of these factors may manifest in a changing baseline, distortion of the signal, experimenting with different electrode arrangements, and others.

The present invention contemplates a new and improved cardiac gating method and apparatus which overcomes the above referenced disadvantages and others.

SUMMARY OF THE INVENTION

In accordance with one aspect of the present invention, a method of magnetic resonance is provided. A region of interest and a region with flowing blood are disposed in a main magnetic field. At least one phase contrast navigator sequence is applied to the flowing blood region to generate navigator echoes. A measurement of blood movement is determined from the navigator echoes and an imaging sequence is gated in accordance with the blood movement measurement.

In accordance with another aspect of the present invention, a magnetic resonance apparatus is provided. A main magnet assembly applies a main magnetic field to an imaging region in which at least a portion of a subject is disposed. A gradient coil assembly applies gradient magnetic fields to a navigation region, spatially encoding dipoles of interest. A radio frequency coil assembly transmits radio frequency pulses into the navigation region, which pulses combine with the gradient pulses to form at least one phase contrast sequence as a navigator for cardiac gating.

One advantage of the present invention resides in the opportunity to perform prospective gating.

Another advantage of the present invention resides in the opportunity to perform retrospective gating.

Another advantage is the elimination of ECG electrodes and other cardiac monitoring hardware from the magnetic field region.

Another advantage resides in gating from a local flow related signal instead of a remote electrical signal.

Another advantage resides in the ability to trigger imaging in all phases of the cardiac cycle.

Another advantage resides in the ability to gate from the blood flow of a fetus.

Another advantage resides in shorter imaging times due to more frequent sampling.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts. The drawings are only for purposes of illustrating a preferred embodiment and are not to be construed as limiting the invention.

DETAILED DESCRIPTION OF THE PREFERRED EMBODIMENT

Figure 1:
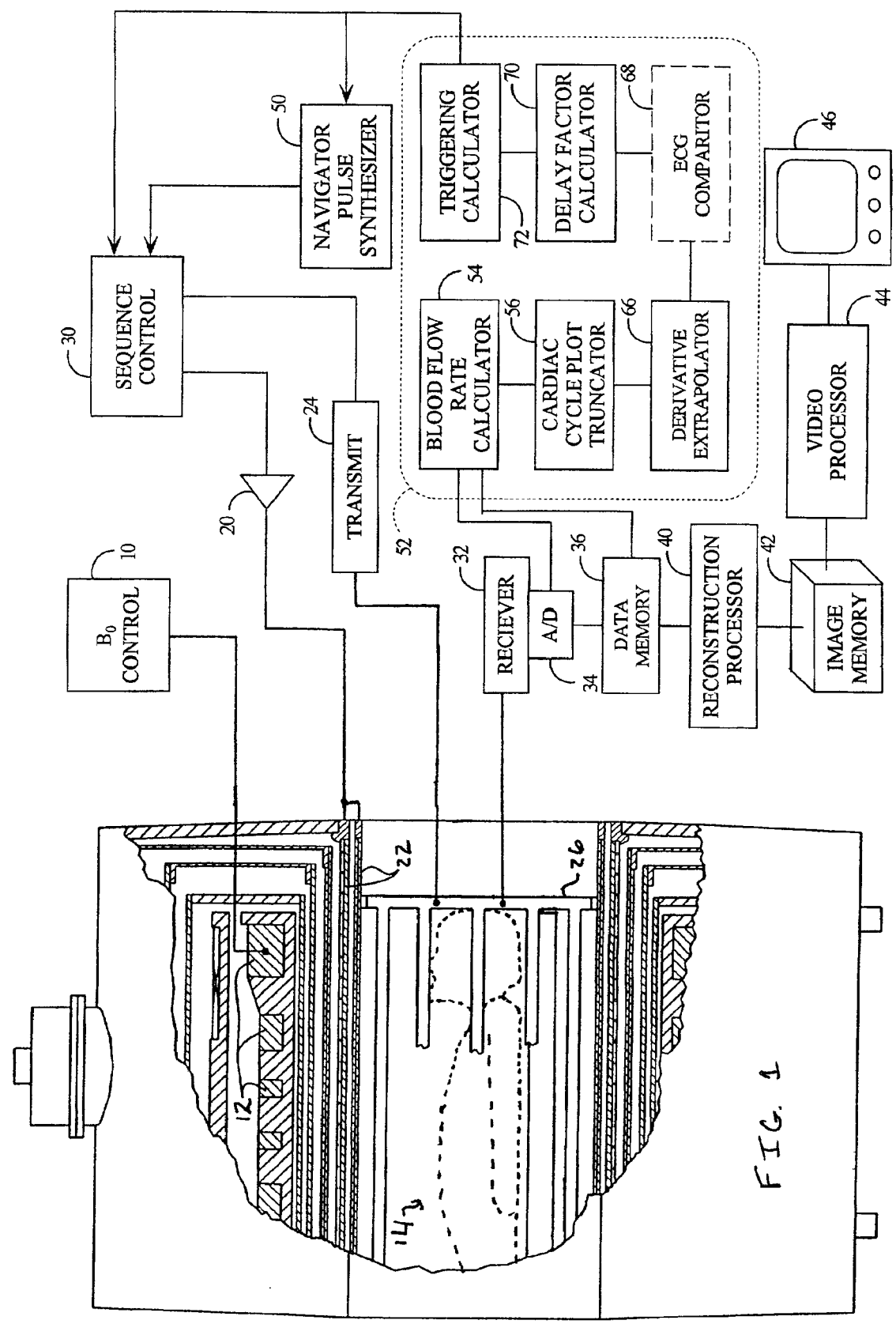
FIG. 1 is a diagrammatic illustration of a magnetic resonance apparatus in accordance with the present invention.

With reference to FIG. 1, a main magnetic field control 10 controls superconducting or resistive magnets 12 such that a substantially uniform, temporally constant main magnetic field is created along a z axis through an examination region 14. A magnetic resonance generation and manipulation system applies a series of radio frequency (RF) and magnetic gradient field pulses to re-orient the magnetization or excite magnetic spins, induce magnetic resonance, refocus magnetic resonance, manipulate magnetic resonance, spatially and otherwise encode the magnetic resonance, to saturate spin, and the like to generate magnetic resonance imaging and spectroscopy sequences. More specifically, gradient pulse amplifiers 20 apply current pulses to selected ones or pairs of whole-body gradient coils 22 to create magnetic field gradients along x, y and z-axes of the examination region 14. A digital radio frequency transmitter 24 transmits radio frequency pulses or pulse packets to a whole-body RF coil 26 to transmit radio frequency $B_1$ fields in the examination region. A typical radio frequency pulse is composed of a packet of immediately contiguous pulse segments of short duration which taken together with each other and any applied gradients achieve a selected magnetic resonance manipulation. The RF pulses are used to saturate, excite resonance, invert magnetization, refocus resonance, or manipulate resonance in selected portions of the examination region. For whole-body applications, the resonance signals are commonly picked up by the whole-body RF coil 26. Optionally, localized coils (not shown) are disposed in the bore more closely adjacent the imaged region.

A sequence control circuit 30 controls the gradient pulse amplifiers 20 and the transmitter 24 to generate any of a plurality of multiple echo sequences such as echo planar imaging, echo volume imaging, gradient and spin echo imaging, fast spin echo imaging, and the like. For the selected sequence, a receiver 32 receives magnetic resonance signals from RF coil 26 and demodulates the signals into a plurality of data lines. If the receiver is analog, an analog-to-digital converter 34 converts each data line to a digital format. Alternately, the analog-to-digital converter is disposed between the radio frequency receiving coil 26 and the receiver 32 for digital receivers. The data lines are stored or buffered in a data memory 36. The data lines are reconstructed into an image representation by a reconstruction processor 40 which applies an inverse Fourier transform or other appropriate reconstruction algorithm. The image may represent a planar slice through the patient, an array of parallel planar slices, a three-dimensional volume, or the like. The image is then stored in an image memory 42 where it is selectively accessed by a video processor 44 that converts slices, projections, or other portions of the image representation into appropriate format for a display, such as a monitor 46 which provides a man-readable display of the resultant image.

In the preferred embodiment, diagnostic imaging sequence is gated off of blood flow. In the preferred embodiment, a diagnostic imaging sequence is gated off blood flow in a selected region or position. A navigator pulse synthesizer 50 synthesizes a cardiac cycle navigator that measures a distribution of flow velocity in a selected region, perhaps a major vessel. The phase contrast navigator N is a Fourier transform of the difference between two acquisitions:

$N$=[signal with flow]–[Reference signal without flow]

$N$=[signal with flow encode gradient]–[Reference signal without flow gradient]

The Fourier transform converts phase encoding of the flow into a velocity distribution. The selected region for the phase contrast navigator can be one-dimensional for a slice, two-dimensional or three-dimensional for a selected volume, preferably with the selected region aligned with the flow encoding gradient. When a phase contrast RF pulse sequence is applied, it excites resonance in a region that includes flowing blood. If the excited region is totally within flowing blood, the phase of the RF signal is proportional to the velocity of the flowing blood. If there is other tissue in the excited region, a reference scan is taken and used to subtract out the static tissue background.

A series of excitations are performed to time map the velocity or flow rate over the cardiac cycle. At a chosen point in the flow cycle (or after a calibrated delay), a conventional imaging sequence is initiated or continued for the selected portion of the flow cycle. The navigator sequence is then applied again to locate the same point in the next cardiac cycle.

More specifically, the blood flow is monitored through the navigation region and a characteristic cardiac cycle plot is constructed. The cardiac cycle plot represents the velocity of the blood flow through the navigation region. In regions close to the heart, such as the ascending aorta, the cardiac cycle plot resembles an ECG signal. The cardiac cycle plot has a large peak that corresponds to the contraction of the left ventricle, at which time blood is flowing quickly through the navigation region. In regions more distal from the heart, the cardiac cycle plot resembles a pulse smoothed by the elasticity of the vessels. If desired, the cardiac cycle plot can be compared to a characteristic ECG signal or a measure of the ECG signal of the subject to refine the correlation therebetween.

Figure 2:
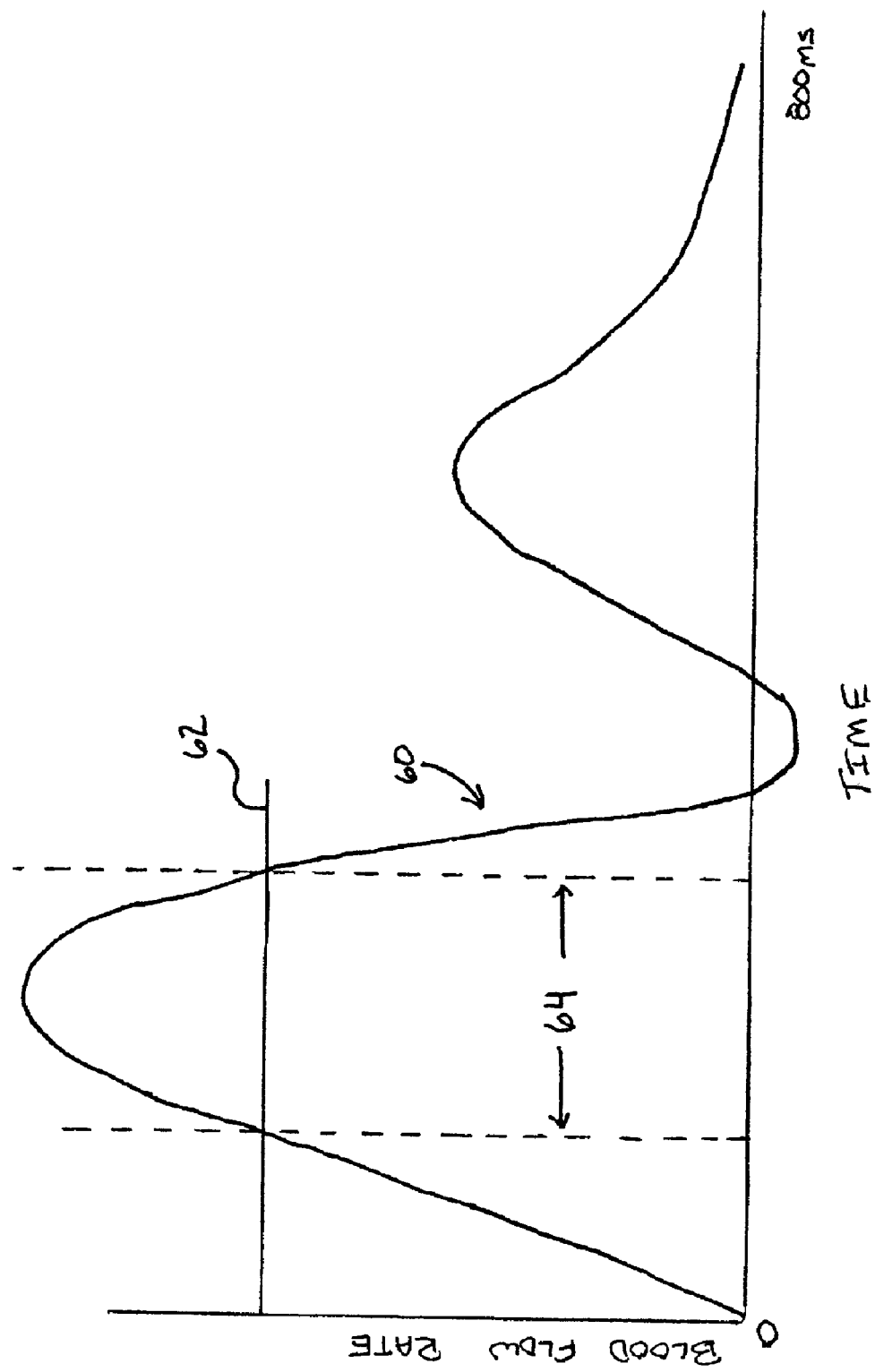
FIG. 2 is an illustration of a typical cardiac cycle plot, in accordance with the present invention.

The cardiac cycle plot is analyzed by a cardiac cycle plot analyzer 52. A blood flow calculator 54 analyzes the navigator echoes and determines blood flow rates. A cardiac cycle plot truncator 56 establishes a flow rate threshold or window. For instance, a diagnostician may only want an image of the region that includes sample times with high blood flow. With reference to FIG. 2, a typical cardiac cycle plot 60 is truncated by a threshold value 62 that sets an imaging time window 64 where the blood flow rate is greater than the threshold value 62. Similarly, the diagnostician might want an image with only low blood flow. Optionally, an independent, fixed time window may be established.

A derivative processor 66 takes a first derivative of the cardiac cycle plot 60. This allows the analyzer 52 to determine at any given point in time whether the flow rate is increasing or decreasing. An optional ECG comparitor 68, as ghosted in FIG. 1, compares the cardiac cycle plot to an ECG signal to determine correlations therebetween. In the preferred prospective embodiment, a delay factor calculator 70 calculates a delay factor that accounts for blood pulse travel time between the navigation region and the imaging region. The length of the delay is largely a factor of the distance between the navigation region and the imaging region. If the imaging region is relatively close to the navigation region, then the delay is relatively short. Likewise, the farther away the two regions spatially, the longer the delay. In prospective gating, the navigation region is typically upstream of the imaging region. The delay represents the time it takes for a pulse of blood (not the blood itself) to travel from the navigation region to the imaging region. When the threshold conditions are met, and the first derivative conditions are met (ascending or descending) in the navigation region and after the calculated delay, an image triggering calculator 72 directs the sequence controller 30 to cease generating navigator echoes and commence diagnostic imaging. Alternately the triggering point can be extrapolated from the amplitude and/or slope of the cardiac cycle plot without setting a threshold or triggering window. A fast spin echo imaging sequence is preferred because only fractions of a second are available for imaging a narrow window in each cardiac cycle, but other sequences are contemplated. Several data lines are collected during the time window 64 in each of a plurality of consecutive cardiac cycles. Navigator echoes are optionally interspersed between fast spin echo repetitions to determine whether the blood flow velocity has moved out of the window 64. For longer imaging windows other imaging sequences, such as echo planar imaging sequences are contemplated. The preferred data collection results in substantially the same blood flow rate through the imaging region throughout the sampling time.

For retrospective gating, navigator echoes are applied over a few cardiac cycles to establish a base line cardiac cycle. Once imaging starts, navigator echoes are interspersed among imaging sequence segments to mark where in the cardiac cycle each data line or group of data lines was collected. For example, navigator and single spin echo sequences are alternated to mark the location of each data line in the cardiac cycle. Alternately, a plurality of data lines are collected between each navigator echo and the cardiac phase of each data line is extrapolated from the base line cardiac cycle. Echo planar, fast spin echo, and other multi-echo sequences are contemplated. Each collected data line and its point in the cardiac cycle are stored in the data memory 36. The operator selects a segment of the cardiac cycle and the corresponding data lines are reconstructed. The cardiac cycle can be divided into a plurality of segments and the reconstructed images displayed sequentially in a ciné mode.

In the prospective and retrospective modes, navigator echoes are preferably applied two or more per cycle to monitor cardiac cycle location. More monitoring points per cycle improve accuracy. Few points may be acceptable for patients with very stable cardiac cycles. Each cardiac cycle, as estimated from the monitored points is compared with the base line cardiac cycle. If a monitored cycle is abnormal, the data collected during it is discarded.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of magnetic resonance comprising:
   disposing a region of interest and a region with flowing blood in a main magnetic field;
   applying at least one phase contrast navigator sequence to the flowing blood region to generate navigator echoes;
   determining a measurement of blood movement from the navigator echoes;
   gating an imaging sequence in accordance with the blood movement measurement.

2. The method as set forth in claim 1, wherein the navigator sequence generates navigator echoes that indicate blood flow velocity.

3. The method as set forth in claim 1, wherein the selected region also includes non-blood tissue and further including:
   acquiring a navigator base line measurement indicative of a contribution of non-blood tissue to the navigator echo.

4. A method of magnetic resonance comprising:
   disposing a region of interest and a region with flowing blood in a main magnetic field;
   repeatedly applying phase contrast navigators over at least one cardiac cycle and determining a plurality of blood movement measurements over the cardiac cycle;
   determining a measurement of blood movement from the navigator echoes;
   generating a blood movement versus time plot indicative of the cardiac cycle from the blood flow measurements;
   gating an imaging sequence in accordance with the blood movement measurement.

5. The method as set forth in claim 4, further including:
   setting a blood flow measurement threshold relative to the cardiac cycle plot to select a portion of the cardiac cycle to be imaged.

6. The method as set forth in claim 4, further including:
   correlating the cardiac cycle plot and electra cardio-graph signals.

7. The method as set forth in claim 4, further including:
   obtaining first derivatives of the cardiac cycle plot.

8. The method as set forth in claim 7, wherein the applied navigator sequences generate navigator echoes that are velocity and acceleration encoded and further including:
   comparing the blood flow velocity and acceleration with amplitudes and derivatives of the cardiac cycle plot to determine points in the cardiac cycle.

9. The method as set forth in claim 8, further including:
   triggering the imaging sequence data acquisition in response to the determined points in the cardiac cycle.

10. A method of magnetic resonance comprising:
    disposing a region of interest and a region with flowing blood in a main magnetic field;
    applying at least one phase contrast navigator sequence to the flowing blood region to generate navigator echoes;
    determining a measurement of blood movement from the navigator echoes;
    applying at least one extrapolation algorithm to the cardiac cycle plot based on the first derivative of the cardiac cycle plot to determine a triggering time; and, triggering a data acquisition of the region of interest at the triggering time.

11. The method as set forth in claim 1 further including:
adjusting the navigator sequence to adjust alignment of the flowing blood region with a blood vessel.

12. A magnetic resonance apparatus comprising:
a main magnet assembly for applying a main magnetic field to an imaging region and a navigation region of a subject;
a gradient coil assembly for applying gradient magnetic fields to the imaging region and the navigation region, spatially encoding dipoles of interest;
a radio frequency coil assembly that transmits radio frequency pulses into the imaging region and the navigation region;
a processor which:
controls the gradient and radio frequency coil assemblies to generate a blood-flow measuring magnetic resonance navigator sequence in the navigation region,
controls the gradient and radio frequency coil assemblies to generate a diagnostic imaging sequence in the imaging region, and
gates the generation of the imaging sequence in the imaging region in accordance with blood flow measured by the navigation sequence in the navigation region.

13. The magnetic resonance apparatus as set forth in claim 12, further including;
a phase contrast sequence synthesizing means for coordinating pulses transmitted by the gradient coil assembly and the radio frequency coil assembly.

14. The magnetic resonance apparatus as set forth in claim 12, further including:
a calculating means that measures a blood flow rate through a blood vessel of interest in the navigation region and obtains a cardiac cycle plot for the blood vessel of interest.

15. A magnetic resonance apparatus comprising:
a main magnet assembly for applying a main magnetic field to an imaging region wherein is disposed at least a portion of a subject;
a gradient coil assembly for applying gradient magnetic fields to a navigation region, spatially encoding dipoles of interest;
a radio frequency coil assembly that transmits radio frequency pulses into the navigation region, which pulses combine with gradient pulses to form at least one phase contrast sequence as a navigator for cardiac gating; and a calculating means that measures a blood flow rate through a blood vessel of interest in the navigation region and obtains a cardiac cycle plot for the blood vessel of interest;
a derivative extrapolation means for obtaining a first derivative of the cardiac cycle plot.

16. The magnetic resonance apparatus as set forth in claim 14, further including:
a comparitor means for comparing the flow rate to an electro-cardiograph and finding similarities therebetween.

17. A magnetic resonance apparatus comprising:
a main magnet assembly for applying a main magnetic field to an imaging region wherein is disposed at least a portion of a subject;
a gradient coil assembly for applying gradient magnetic fields to a navigation region, spatially encoding dipoles of interest;
a radio frequency coil assembly that transmits radio frequency pulses into the navigation region, which pulses combine with gradient pulses to form at least one phase contrast sequence as a navigator for cardiac gating; and,
a calculating means that measures a blood flow rate through a blood vessel of interest in the navigation region and obtains a cardiac cycle plot for the blood vessel of interest;
a triggering time calculating means for:
applying an extrapolation algorithm to the cardiac cycle plot;
combining the extrapolated data with first derivative criteria;
computing a triggering time; and,
triggering a data acquisition of the region of interest at the triggering time.

18. A magnetic resonance apparatus comprising:
generating a magnetic field through a region of interest and a region with flowing blood in a main magnetic field;
a means for applying at least one phase contrast navigator sequence to the flowing blood region to generate navigator echoes;
a means for measuring blood movement from the navigator echoes in the flowing blood region;
a means for gating an imaging sequence in accordance with the measured blood movement.

* * * * *